(12) United States Patent
Latta

(10) Patent No.: US 10,639,242 B1
(45) Date of Patent: May 5, 2020

(54) DIMETHICONE-BASED ORAL VARNISH

(71) Applicant: Inspired Material Solutions, LLC, Omaha, NE (US)

(72) Inventor: Mark A. Latta, Omaha, NE (US)

(73) Assignee: Inspired Material Solutions, LLC, Omaha, NE (US)

( * ) Notice: Subject to any disclaimer, the term of this patent is extended or adjusted under 35 U.S.C. 154(b) by 0 days.

(21) Appl. No.: 16/674,854

(22) Filed: Nov. 5, 2019

Related U.S. Application Data

(60) Provisional application No. 62/755,705, filed on Nov. 5, 2018.

(51) Int. Cl.
| | | |
|---|---|---|
| *A61K 6/20* | (2020.01) | |
| *A61Q 11/00* | (2006.01) | |
| *A61K 6/60* | (2020.01) | |
| *A61K 6/69* | (2020.01) | |
| *A61K 6/70* | (2020.01) | |
| *A61C 19/06* | (2006.01) | |

(52) U.S. Cl.
CPC ............... *A61K 6/20* (2020.01); *A61K 6/60* (2020.01); *A61K 6/69* (2020.01); *A61K 6/70* (2020.01); *A61Q 11/00* (2013.01); *A61C 19/063* (2013.01)

(58) Field of Classification Search
CPC ............. A61K 7/16; A61K 7/20; A61Q 11/00
USPC ...................... 424/49, 52, 53, 401
See application file for complete search history.

(56) References Cited

U.S. PATENT DOCUMENTS

| | | | |
|---|---|---|---|
| 7,264,882 B2 | 9/2007 | Engelbrecht | |
| 2004/0033205 A1* | 2/2004 | Date ................... | A61K 8/0208 424/53 |
| 2014/0105941 A1* | 4/2014 | McHale ............... | A61K 8/90 424/401 |
| 2015/0366786 A1 | 12/2015 | Huo et al. | |

FOREIGN PATENT DOCUMENTS

| | | | | |
|---|---|---|---|---|
| WO | WO2001/01940 | * | 1/2001 | ............ A61K 7/16 |
| WO | WO/2014/059143 A1 | | 4/2014 | |

OTHER PUBLICATIONS

"International Search Report issued in International Application No. PCT/US2019/059830 dated Feb. 28, 2020", Feb. 28, 2020.
"Polydimethylsiloxane", Wikipedia, Oct. 12, 2018, https://en.wikipedia.org/w/index.php?title=Polydimethylsiloxane&oldid=863655868.

* cited by examiner

*Primary Examiner* — Walter E Webb
(74) *Attorney, Agent, or Firm* — Vos-IP, LLC

(57) ABSTRACT

An oral varnish comprising a combination of two different viscosity dimethicone components, wherein the difference between the two different viscosity dimethicone components is about 2.0 million cP or greater; and comprising at least one active ingredient, which is preferably a fluoride donor.

6 Claims, 2 Drawing Sheets

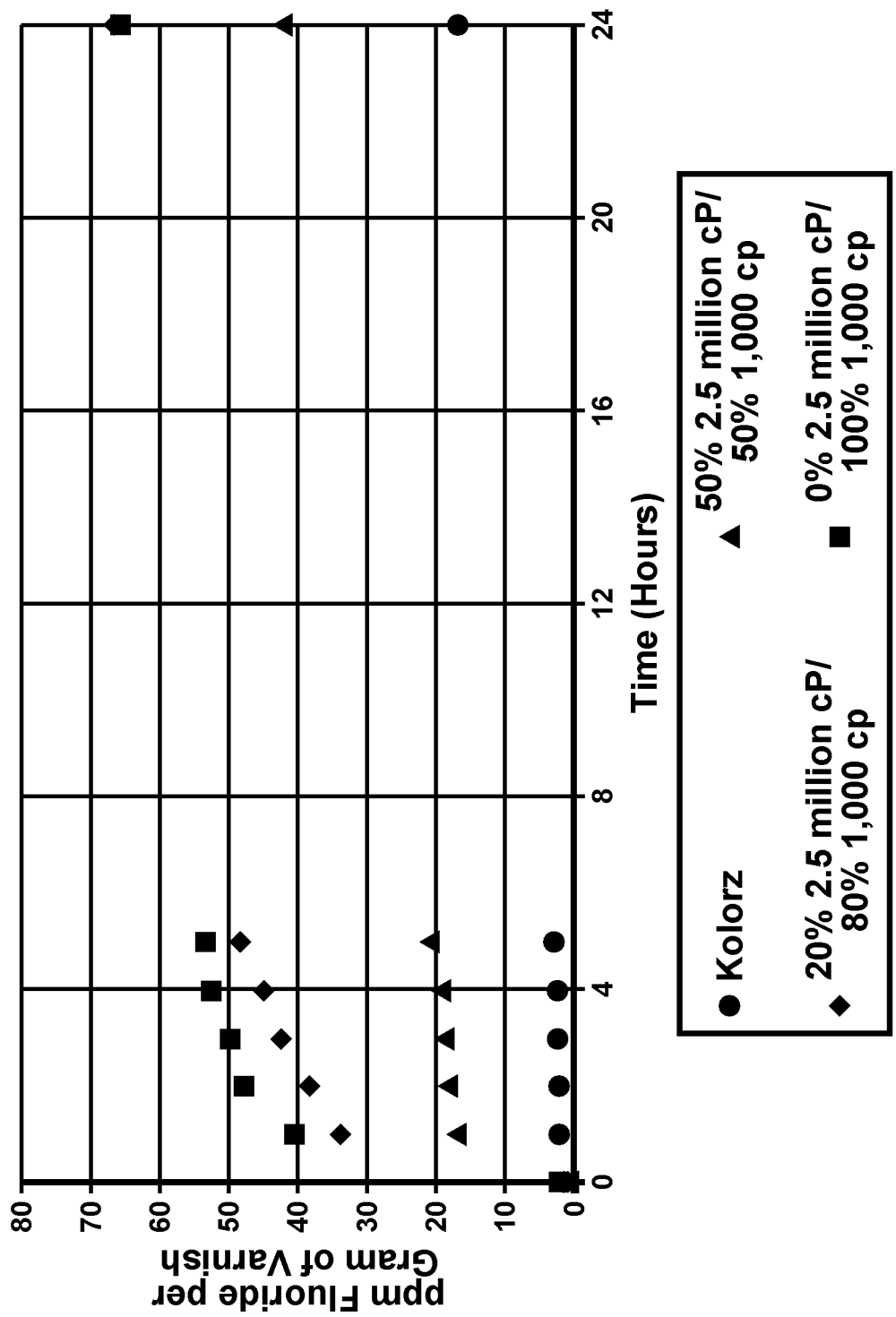

DIMETHICONE-BASED ORAL VARNISH

CROSS-REFERENCE TO RELATED APPLICATIONS

This application claims the benefit of U.S. Provisional Patent Application No. 62/755,705 filed on Nov. 5, 2018 with the US Patent and Trademark Office, the contents of which are incorporated herein by reference in their entirety.

FIELD OF INVENTION

The present invention is generally related to oral varnishes, suitable for oral use, and particularly for providing an additive or therapeutic to the oral mucosa.

BACKGROUND OF THE INVENTION

Varnishes based on natural resins have been used since ancient times to produce solid transparent or semitransparent coatings with protective and/or decorative properties. Among the natural resins, rosin has found widespread use in varnishes because of its inherent properties such as water repellency, abrasion resistance, adhesiveness, film formation, and integrity, which it imparts to coatings.

Rosin and its derivatives are particularly attractive for use in varnishes applied to humans and animals based on a historical safety profile. They have a long history as additives in chewing gum and personal care products. They are used as direct additives in foods and inactive ingredients in topical and oral pharmaceuticals. Rosin-based varnishes are useful when a removable, water-insoluble coating with good adhesion to human or animal tissue is required. They are particularly attractive when the varnish may be ingested or otherwise enter the body.

Because of their ease of application and excellent coating properties, varnishes are useful in dental applications. A dental varnish may act as a barrier alone or it may additionally contain a therapeutic agent or other additive for oral delivery. Currently, most dental varnishes are spirit varnishes, wherein a film forming, water-insoluble resin or polymer (natural or synthetic) is dissolved in a pharmaceutically acceptable solvent and applied to the desired tooth area. Varnishes that are most desirable do not require thorough drying of the teeth before application. The solvent evaporates and/or is extracted by saliva to leave a coating that remains on the tooth surface for a period of time, preferably at least several hours, though in practice, the actual time is often greatly reduced due to removal by the tongue and other mechanical removal.

Commercial dental varnishes are well known in the art. The first dental varnishes, used to coat prepared cavity walls prior to placement of restorative materials, were based on natural copal resins dissolved in chlorinated hydrocarbons and are still used to prevent penetration of restorative materials into dental tissue.

Particularly useful dental varnishes contain fluoride, which are usually administered to patients who are at high risk for dental carries. Fluoride varnishes are approved by the FDA as medical therapeutic for use as cavity preparation liners and for the treatment of hypersensitive teeth.

Despite the numerous benefits of dental varnishes, they still have limited use on dental patients compared to fluoride gels, foams, and rinses. An important disadvantage of traditional sodium fluoride varnishes based on natural resins is that the yellow to brown color of the natural resin causes a temporary change in tooth color. This undesirable characteristic limits patient acceptance of these natural resin varnishes and has promoted efforts to make varnishes based on modified natural resins in more acceptable lighter colors to increase patient acceptance.

Modified rosins that have been esterified and/or hydrogenated are available commercially in certain light colors. These modified rosins can produce a near colorless varnish. Unfortunately, compared to natural rosin, these materials have significantly lower solubility in solvents that are pharmaceutically acceptable for oral use. Ideally, solvents used in preparations that enter the body have acceptable taste, irritation, toxicity, and allergic reaction (sensitization) profiles. The most commonly used solvents in oral preparations requiring water miscibility are ethanol, glycerin, propylene glycol, and PEG 300 & 400. Applications for water immiscible solvents most often use liquid paraffin and vegetable oils. For topical use, saturated aliphatic hydrocarbons, ether, and isopropanol, among others, are also acceptable solvents.

Although a dental varnish is topical in its application, its prolonged residence in the oral cavity results in unavoidable and unintended ingestion, particularly the portion of the solvent that does not evaporate during the initial application. The ideal solvent, therefore, is low in toxicity, volatile enough to allow rapid drying of the varnish, water soluble, and extractable by bodily fluids, such as saliva. Since ethanol possesses these properties, it is a preferred solvent for applications where the varnish may enter the body, such as dental varnishes.

In certain varnishes, natural resins are replaced by certain food grade shellacs. Both the shellac-based and resin-based varnishes have shown to have similar efficacy when using fluoride at 5% and 2.5% sodium fluoride concentrations. However, these shellac-based products still possess certain limitations, including solubility, taste, and other performance limitations, which have limited their global use.

Generally, however, oral varnishes show great efficacy for reducing sensitivity, and off label use for remineralization in patients of all ages, including among children under 6, between 6-18 years, and adult populations is widespread. Yet, the several drawbacks to these products have reduced or minimized the use of these products, in what should otherwise be much more frequent use.

Accordingly, herein are described the creation of new products to create safe, reliable, and highly efficacious oral varnish products for application to tooth and oral mucosal surfaces, where the oral varnish includes therapeutic and other excipients that can repair or reduce caries, and otherwise treat oral tooth and mucosal surfaces.

SUMMARY OF THE INVENTION

In a preferred embodiment, an oral varnish comprising between 25-99% of a 12,500 cP dimethicone and between 1% and 75% of a 2.5 million cP dimethicone; and a 5% Sodium Fluoride. In preferred embodiments, the 2.5 million cP dimethicone is between 1 and 50%.

In a further embodiment, an oral varnish comprising between 25-99%/o of a 1,000 cP dimethicone and between 1% and 75% of a 2.5 million cP dimethicone; and a 5% Sodium Fluoride.

In certain embodiments, there is a 2.5% Sodium Fluoride, or other Fluoride donor material. In certain embodiments, there is a 5.0% Sodium Fluoride weight percentage, or equivalent from another Fluoride donor. Concentrations for OTC-based products have dramatically lower concentration of Fluoride as compared to the oral varnish of the present disclosure. Where OTC is at a 1500 ppm concentration, the varnish here, when stated in ppm is typically greater that 20,000 ppm and can be up to about 50,000 ppm.

In a preferred embodiment, an oral varnish comprises a first and second dimethicone, said first dimethicone having a viscosity between 1,000 and 25,000 cP, and a second dimethicone having a viscosity of between 2.0 million cP and 3.0 million cP; and a fluoride component having a concentration of fluoride of between 2.5 and 5.0%. In certain embodiments, the fluoride component is selected from the group consisting of: sodium fluoride, stannous fluoride, sodium monofluorophosphate, ACPF, or combinations thereof. In certain embodiments, the concentration of the fluoride donor is between about 15,000 ppm and 50,000 ppm fluoride. In certain embodiments, the concentration of the fluoride donor is between about 20,000 ppm and 50,000 ppm fluoride.

An oral varnish comprising two dimethicone polymers and a fluoride; a first dimethicone polymer having a formula of $Me_3$-O-$[SiMe_2]n$-$Me_3$ wherein n is a number of repeating units, having a viscosity of between about 1,000 and 25,000 cP, and a second dimethicone polymer having a formula wherein "n" is larger than the first dimethicone polymer, and having a thicker viscosity of between about 2.0 million cP and 3.0 million cP; with the first dimethicone polymer comprising between 10 and 99 percent of the total mass of the formulation and said second dimethicone polymer comprising between 1 and 90 percent of the total mass of the formulation.

An oral varnish comprising two dimethicone polymers, and a fluoride; a first dimethicone polymer having a formula of $Me_3$-O-$[SiMe_2]n$-$Me_3$ with "n" repeating units, and a second dimethicone polymer having a greater viscosity and more "n" repeating units than the first dimethicone polymer; with the first dimethicone polymer in a ratio with the second dimethicone polymer of between 100:1 to 0.5:1. In certain embodiments, preferably the ratio is between about 55:1 to about 1:1, or about 40:1 to about 1:1.

An oral varnish of the above embodiments, wherein the Fluoride donor agent is at the maximum allowable for an over-the-counter product. In preferred embodiments, the Fluoride is selected from the group consisting of: sodium fluoride, stannous fluoride, sodium monofluorophosphate, amine fluoride 297, and combinations thereof.

A method for formulating the compositions of any of the above embodiments comprising: admixing together a first and second dimethicone with a fluoride ion donor; adding an amount of said first dimethicone, wherein said first dimethicone has a viscosity of between 1,000 cP and 25,000 cP; adding to said first dimethicone an amount of a fluoride ion donor to meet an over-the-counter or a prescription strength; mixing the components using a centrifugal mixer; adding a first portion of the second dimethicone, said second dimethicone having a viscosity between 2.0 million and 3.0 million cP and mixing with said first dimethicone and said fluoride ion donor; and adding a second portion of the second dimethicone.

In certain embodiments, the second dimethicone is admixed in a single portion, or in 2, 3, 4, 5, 6, 7, 8, 9, 10, or more portions to allow for mixing of the materials. In preferred embodiments, the portions as admixed are in equal amounts.

In a further embodiment, a dimethicone-based oral varnish comprising a first dimethicone material having a viscosity of between about 1,000 cP and 25,000 cP, and a second dimethicone material having a viscosity of between about 2.0 million and 3.0 million cP; and at least one active agent. In one embodiment, wherein the active agent is a fluoride agent.

In one embodiment, wherein the fluoride agent is selected from the group consisting of sodium fluoride, stannous fluoride, ACPF (amorphous calcium phosphate fluoride), sodium monofluorophosphate, amine fluoride 297, and combinations thereof.

In one embodiment, wherein the ratio of the first dimethicone to the second dimethicone is between 40:1 and 1:2.

In one embodiment, wherein the ratio of the first dimethicone to the second dimethicone is between 25:1 and 1:1.

In one embodiment, wherein the ratio of the first dimethicone to the second dimethicone is between 20:1 and 1:1.

In one embodiment, the oral varnish further comprising a phosphate donor, wherein said phosphate donor is selected from the group consisting of: potassium phosphate monobasic, potassium phosphate dibasic, dicalcium phosphate, tricalcium phosphate, sodium phosphate monobasic, sodium phosphate dibasic, monomagnesium phosphate, dimagnesium phosphate, and combinations thereof.

In one embodiment, the oral varnish further comprising a calcium donor selected from the group consisting of: calcium nitrate, calcium chloride, calcium citrate, calcium sulfate, calcium oxalate, calcium fluoride, dicalcium phosphate, tricalcium phosphate, calcium gluconate, and combinations thereof. In a further embodiment, the calcium donor may further include at least one amino acid. In a further embodiment, wherein the amino acid is lysine.

In one embodiment, the oral varnish further comprising a flavorant or a sweetener selected from the group consisting of: spearmint oil, wintergreen oil, peppermint oil, bubblegum, cherry, vanilla, chlorophyll, acesulfame K, sucralose, xylitol, saccharin, sodium cyclamate, natural or synthetic flavorant or sweetener, and combinations thereof.

In one embodiment, the oral varnish further comprising an antimicrobial agent selected from the group consisting of: benzalkonium chloride, cetylpyridinium chloride, trans-farnesol, chitosan, chlorhexidine, quaternary ammonium compounds, phenols, bisguanides, and combinations thereof.

In one embodiment, the oral varnish further comprising one or more of a bulking agent, a flowing agent, a preservative, or combinations thereof. As with the inclusion of a flavorant, it may be suitable to provide a small amount of a bulking agent or texturizing agent to the product to impart a tactile feel to the material, or to improve its consistency for application to the tooth surfaces. For example, patients may prefer to have a slight texture on the material to allow for a patient to "feel" like the material remains on the surfaces of the oral mucosa. Bulking agents may be necessary to simply provide for a superior consistency and overall feel to the product. A flowing agent or glidant may similarly be added to the compositions herein to impart modify the physical properties of the material. For example, magnesium stearate, stearic acid, silicon dioxide, glycerin, palmitate, and others known to those of ordinary skill in the art.

A further embodiment is directed towards a method of formulating any of the oral varnish products described above comprising placing the entirety of the first dimethicone component into a mixing container and adding into it an amount of a fluoride donor; mixing the two components at 3,000 RPM for about 10 minutes in a centrifugal mixer, after the mixing step adding into the mixed two components the second dimethicone, wherein 4 of the total mass of the second dimethicone added in five different increments, each increment individually mixed at 3,000 RPM for five minutes before addition of a further increment, until all of the second dimethicone is added and mixed into the formulation.

In one embodiment, the method further comprising adding a calcium donor with the first dimethicone and the fluoride donor before mixing the components.

In one embodiment, the method further comprising adding an antimicrobial agent. In a preferred embodiment, wherein the antimicrobial agent is benzalkonium chloride or cetylpyridinium chloride with the first dimethicone and fluoride before mixing the components.

In one embodiment, the method further comprising adding a bulking agent, a flowing agent, a preservative, or combinations thereof with the fluoride agent.

In one embodiment, an oral varnish comprising a first dimethicone material having a viscosity between 1,000 cP and 25,000 cP, and a second dimethicone material having a viscosity of between about 2.0 million and 3.0 million cP and at least one active agent. In a further embodiment, the oral varnish wherein the at least one active agent is a fluoride donor having a concentration of between 2.5 and 5.0% weight percent fluoride.

In a further embodiment, the oral varnish wherein the fluoride donor is selected from the group consisting of sodium fluoride, stannous fluoride, sodium monofluorophosphate, ACPF, amine fluoride 297, and combinations thereof. In a further embodiment, the oral varnish wherein the ratio of the first dimethicone to the second dimethicone is between 100:1 and 1:8. In a further embodiment, the oral varnish wherein the concentration of the fluoride donor yields a concentration of fluoride between 15,000 ppm and 50,000 ppm.

In a further embodiment, the oral varnish further comprising a phosphate donor. In a further embodiment, the oral varnish further comprising a calcium donor. In a further embodiment, the oral varnish further comprising a comprising a flavorant or a sweetener. In a further embodiment, the oral varnish further comprising an antimicrobial agent selected from the group consisting of: benzalkonium chloride, cetylpyridinium chloride, and combinations thereof. In a further embodiment, the oral varnish further comprising one or more of a bulking agent, a flowing agent, a preservative, or combinations thereof. In a further embodiment, the oral varnish wherein the bulking agent is an edible wax. In a further embodiment, the oral varnish further comprising L-lysine.

In a further embodiment, a method of formulating a dimethicone based oral varnish comprising a first dimethicone material having a viscosity between 1,000 cP and 25,000 cP, and a second dimethicone material having a viscosity of between about 2.0 million and 3.0 million cP and a fluoride donor, comprising adding the first dimethicone component into a mixing container and adding into it an amount of the fluoride donor; mixing the two components at 3,000 RPM for about 10 minutes in a centrifugal mixer, after the mixing step, adding into the mixed two components a portion of the second dimethicone, wherein a portion of the total mass of the second dimethicone added in at least two increments, each increment individually mixed at 3,000 RPM for five minutes before addition of a further increment, and adding a portion of the second dimethicone until all of the second dimethicone is added and mixed into the formulation.

In a further embodiment, the method further comprising at least one active ingredient. In a further embodiment, the method, wherein the one active ingredient comprises a calcium donor with the first dimethicone and the fluoride donor before mixing the components. In a further embodiment, the method wherein the one active ingredient is an antimicrobial agent, and wherein the antimicrobial agent is added with the first dimethicone and fluoride donor before mixing the components. In a further embodiment the method, further comprising adding a bulking agent, a flowing agent, a preservative, or combinations thereof with the fluoride donor. In a further embodiment, the method, wherein the antimicrobial agent is selected from the group consisting of: benzalkonium chloride, cetylphyrdimium chloride, and combinations thereof.

In a further embodiment, an oral varnish consisting essentially of a first dimethicone material having a viscosity of between 1,000 cP and 25,000 cP, and a second dimethicone material of between about 2.0 million and 3.0 million cP; a fluoride donor providing a fluoride concentration of between 15,000 and 50,000 ppm within the oral varnish, and at least one active agent, wherein the first and second dimethicone materials are provide at a ratio of between 100:1 and 1:8.

In a further embodiment, an oral varnish consisting of a first dimethicone material having a viscosity between 1,000 cP and 25,000 cP, and a second dimethicone material of between about 2.0 million and 3.0 million cP; a fluoride donor and at least one additional excipient. In a further embodiment, the oral varnish, wherein the first and second dimethicone are at a ratio of between 40:1 to 1:8 of the first to the second dimethicone material. In a further embodiment, the oral varnish wherein the at least one additional excipient is selected from the group consisting of: a bulking agent, a flowing agent, a preservative, a flavorant, or a sweetener. In a further embodiment, the oral varnish wherein the active agents are selected from the group consisting of: a fluoride donor, a phosphate donor, a calcium donor, benzalkonium chloride or cetylpyridinium chloride, and combinations thereof.

A method of manufacturing a dimethicone-based fluoride varnish comprising: adding a first dimethicone component into a mixing container and adding into it an amount of a fluoride donor; mixing the two components at 3,000 RPM for about 10 minutes in a centrifugal mixer, after the mixing step adding into the mixed two components a second dimethicone component, said second dimethicone component having a greater viscosity than said first dimethicone component, and wherein said second dimethicone component is added to the mixing container in at least two increments, each increment individually mixed at 3,000 RPM for five minutes before addition of a further increment, until all of the second dimethicone is added and mixed into the formulation. In a preferred embodiment wherein the fluoride donor is added at a concentration of at least 15,000 ppm.

BRIEF DESCRIPTION OF THE FIGURES

FIG. 2 depicts a release profile of several different blends of the present disclosure, about release of fluoride over a 24-hour period.

DETAILED DESCRIPTION OF THE INVENTION

Figure 1:
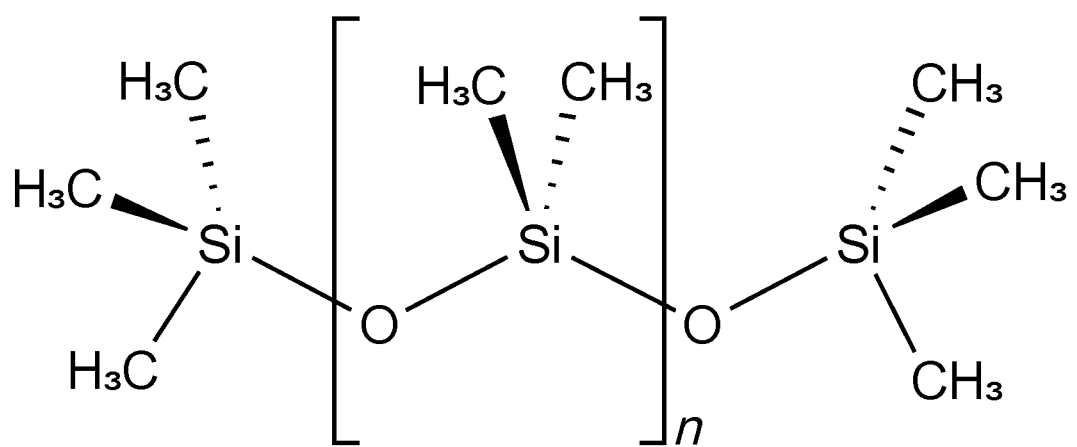
FIG. 1 depicts a figure of the formula of PDMS (Dimethicone) having n number of repeating siloxane units.

The oral mucosa is constantly attacked by sugars, alcohols, low and high pH foods and beverages, and materials that stain or damage tooth, enamel, and the gums of individuals. Herein, certain embodiments describe a new and useful oral varnish for treatment of several ailments of the oral mucosa. Specific therapeutic uses are targeted at reduction in the incurrence of caries and dentin sensitivity, however, in certain embodiments, there may also be suitable materials for the treatment of bacterial, viral, and fungal infections, dry mouth, and a number of other specific ailments described herein.

Indeed, each of these issues, alone, are significant issues faced by both individuals and by dental professionals treating the individuals. The ability to reduce caries, or to reduce dentin sensitivity would have wide ranging applications for a multitude of patients, including children with immature teeth and including children and adults with mature teeth.

Traditionally fluoride varnish includes a carrier of resin-based material, an alcohol or other solvent, and fluoride. This material is painted onto a tooth surface and then it dries with a yellow or brownish color. This coloration frequently means that such use is limited or excluded for all patients for daytime use, and thus many potential patients eschew the treatment because of aesthetics and social acceptability.

Certain fluoride varnishes have replaced the resin-based carrier with other materials, yet these have other issues that prevent their common use. Finally, many of the varnishes have also introduced a colorant or flavoring agent as ways to mask or improve the visual concern, but also to improve the taste of the material.

A potential issue with the addition of a flavorant is that it may increase the rate of the material being washed away from the tooth surfaces, and thus reduce the time the fluoride is present on the tooth or adjacent to or on the gums of the patient. While saliva flow is necessary in many cases to ensure remineralization and desensitization to all tooth, dentin, and gum surfaces, a rapid wash out of the material reduces the efficacy of the product. Finally, a rough texture of the material itself, due to the resin-based product, is often uncomfortable to many users, and results in tongue action to the material thereby increasing the rate of wash out. Still others may simply brush the tooth surfaces to get relief from the uncomfortable texture, discoloration appearance, or unpleasant taste of the materials.

A primary use of these materials is for tooth remineralization. While this is typically an off-label use, the high concentration of fluoride is shown to dramatically prevent the incidence of caries for both immature and mature tooth surfaces when fluoride is applied at a dental visit. Typically, dental varnishes are applied to a tooth surface after the teeth have been cleaned. Cleaning, or prophylaxis, is the removal of tartar (mineralized plaques) from tooth surfaces. In certain cases, this includes tooth scalene, polishing, and debridement of tartar from the tooth surface. Once the tooth surfaces are free of tartar, the dental resin is applied. The concentration of fluoride or other additives or therapeutics is typically between about 1.5%-10% sodium fluoride, of the total weight of the product. For example, a typical fluoride percentage would be between about 1.5% to about 10% (depending on the fluoride donor) and often range from about 20,000 ppm to about 50,000 ppm fluoride. Thus, these concentrations are significantly higher than concentrations of OTC toothpastes and remain severalfold higher than concentrations of prescription strength toothpastes which usually range from about 600-5000 ppm.

For example, a prescription strength fluoride varnish product is painted on each tooth surface and remains in place for usually about 1 to 8 hours, with a typical treatment having the varnish on the tooth surface for between 4 to 6 hours. Eating and drinking of a limited diet is acceptable with most varnish but brushing of the tooth surfaces or other food or drink materials that rub the tooth surfaces will remove the varnish.

The new fluoride varnish developed herein utilizes concentrations of fluoride at or above 1.5% sodium fluoride, with preferable concentrations at 2.5 or 5.0% sodium fluoride. The new fluoride varnish removes the yellow or brown like coloration that is problematic for most users because of cosmetic appearances, and it also eliminates or reduces the uncomfortable taste and texture for the resin-based varnishes. Indeed, the fluoride varnish described herein leaves a smooth coating on tooth surfaces and can be flavored with any number of flavorants. As described herein, a fluoride varnish is provided that preferably combines two different viscosity dimethicone products that heretofore, were unable to be mixed, with additional additives, excipients, therapeutics, and a fluoride ion donor.

Furthermore, the embodiments of the present disclosure detail a material that is free from rosin, does not require the use of an alcohol as a solvent, and is aqueous free. Indeed, the ability to remove the rosin and the solvent provides for new products for those who are allergic to rosin, or those sensitive to the alcohol residuals from existing products. The embodiments herein allow for formation of a carrier that is highly adhesive to tooth and oral mucosal surfaces and allows for carrying of active agents to precipitate onto tooth surfaces. As used herein, the terms additive and excipient are used interchangeably and include any material added to the varnish product of the present embodiments other than the dimethicone components. This term includes additional excipients and therapeutic agents, but also includes binders, preservatives, alcohols, titanium dioxide, sweetener, dimethacrylates, rosin, flavorants, colorants, and the like that may be suitable for dispersion from the varnish.

As used herein, the term therapeutics means, therapeutic compounds which provide a medicinal, healing, or therapeutic effect to at least one cell in the oral mucosa as understood by those of skill in the art. For example, a therapeutic as used with the present embodiments may include, but is not limited to: calcium, phosphate, and or fluoride-based products or donors for use in the oral mucosa as understood by those of skill in the art, and other antimicrobial agents, healing agents, and the like that impart the therapeutic effect to at least one cell. Nonlimiting examples include sodium fluoride, difluorosilane, stannous fluoride, APF (acidulated phosphate fluoride) ACPF (amorphous calcium phosphate fluoride), ACP (Amorphous calcium phosphate), sodium monofluorophosphate, benzalkonium chloride, potassium phosphate dibasic, calcium compounds, calcium nitrate, and cetylpyridinium chloride.

In preferred embodiments, an oral fluoride varnish comprises a first dimethicone product having a first viscosity. FIG. 1 details a generic formula for dimethicone, with "n" number of repeating units. The greater the number of repeating "n" units, the greater the viscosity of the material. The oral varnish further comprises a second dimethicone product, having a second viscosity, wherein the second dimethicone product's viscosity is at least 2.0 million cP greater than the viscosity of the first dimethicone product. The cP unit (centipoise) is a unit of dynamic viscosity. The combination of the two viscosities provides a material that, when applied to a tooth surface, provides for a barrier, and has strong mucoadhesive properties, wherein the material will adhere to the tooth surface and is resistant to being removed because of strong adhesion. However, it also serves as a reservoir for excipients for treatment of one or of many of the afflictions described herein.

Oral fluoride varnishes are developed to adhere to tooth and oral mucosal surfaces, where the varnish itself serves as a reservoir for therapeutics, typically fluoride, to allow for remineralization of tooth surfaces. Indeed, as depicted in FIG. 2, the graph provides values for release of fluoride of between about 2.5 and 5.0% sodium fluoride (or equivalent fluoride donor) based upon three different formulations, one having 1:1 ratio of 2.5 million cP and 1,000 cP dimethicone, a second having 1:4 ratio of 2.5 million and 1,000 cP dimethicone, and a third at 100% 1,000 cP dimethicone. As a control an existing fluoride varnish, Kolorz™ clearshield 5% sodium fluoride varnish was provided.

Time and release profile are both instrumental in allowing the fluoride to leave the carrier and to remineralize on tooth surfaces. Table 3, below, details several different formulations of the present disclosure, each having a different amount of forces (peak adhesive forces) and (total work of adhesion) which provide for a value of each material with respect to its adhesive forces. Those with a greater adhesion are going to typically remain on a tooth surface for a greater period of time than one with a lower peak adhesive force. Accordingly, formulations using a greater concentration of the higher viscosity dimethicone show an increased adhesion.

At the same time, there must be a balance between the peak adhesive forces and the rate of dissolution of the fluoride from the material. FIG. 2 provides that those with lower amounts of the 2.5 million cP dimethicone have a slower dissolution rate of the fluoride from the carrier. At a 1:1 ratio the fluoride release rate is nearly half of that with the other two tested release profiles of the present disclosure. However, this formulation still had a dramatically higher release profile as compared to the Kolorz™ product. Accordingly, while the product with only the 1,000 cP dimethicone had the fastest release profile from 0-5 hours, at 24 hours, its total release was nearly identical to that of the 1:4 ratio product. And, the 1:4 ratio product has a dramatic and significant improvement in adhesion when compared to the 1,000 cP material. The cP unit (centipoise) is a unit of dynamic viscosity.

At 24 hours, the release profile of the 1:1 ratio product reached over 40 ppm fluoride per gram of varnish. The importance of these release profiles is to evaluate the two-fold concern of a release rate that allows for uptake of the released fluoride, while balancing the need for adhesion to maintain the material on a tooth or oral mucosa surface. For example, if the 1,000 cP material alone washes off a tooth surface in 30 minutes, its fast rate of release is not sufficient because it would not have sufficient time to remineralize. Similarly, too fast of a release may simply release minerals into saliva and not onto a tooth surface. Thus, a slightly slower release may benefit and ultimately exceed a fast release, when considering the adhesion to a tooth surface.

The oral varnish of the present disclosure must also have a profile that allows for application of the material at room temperature. Indeed, ease of application is necessary to ensure that the material is correctly applied, but also to aid in its ultimate use. A material that needs to be heated or chilled or applied with special applicators is likely to face burden from the professionals who will apply these materials, and thus the benefit of the product will remain in the drawer, unused, instead of on a tooth surface. Thus, the material is preferably a gel, or paste, which can be brushed or painted onto a tooth surface, as one would typically find from currently available toothpastes and tooth gels for oral application. Finally, the material, once in contact with saliva generally remains adhered to the tooth surface to ensure that the material remains in contact with the tooth surface or oral mucosa for sufficient amount of time to enable the release of the ions within the material.

A primary concern of commercial varnishes is their use of natural resins. These natural resins require an alcohol or other solvent for application and then leave a yellow or brown film on the tooth surface. This is realistically an aesthetic issue, but for children, adolescents, and adults who use such products, there is often a reluctance to maintain the product on tooth surfaces for the necessary duration to allow for the transfer of the fluoride to tooth surfaces. Thus, the material is rubbed off, by washing, brushing, flossing, or simply by tongue action. Indeed, the existing resin-based varnishes also suffer from a tactile feel on tooth surfaces that feels dirty, or grimy, and thus imparts tongue action to the tooth surfaces, which ultimately removes the varnish at an increased rate. The present embodiments comprise a varnish that has a clear color after application to the tooth surface and thus eliminates the brown or yellow coloration present in many of the resin-based materials.

Furthermore, the use of the dimethicone materials, provides for a smooth and clean tactile coating on tooth surfaces. Indeed, dimethicone products are frequently used for their ability to act as a lubricant or smooth texture. Thus, by creation of a smooth surface on the tooth surfaces, there will be a reduction in tongue movement, and thus reduce the removal of the dimethicone-based formulations of the present disclosure as compared to those that rely upon natural resins as a carrier. By reducing the removal of the formulations, naturally there will be an increase in the time that the material is on the tooth surfaces and thus an improvement of release of the materials to the tooth surface and oral mucosa.

As oral varnishes have a long and safe profile of use, the application of fluoride components in the presently disclosed concentrations is not expected to pose any safety risk. Furthermore, as provided herein, the FDA has previously approved several dimethicone materials for use in oral products. Accordingly, the primary components have an understood safety profile for their uses in oral applications.

Components of Oral Varnishes of the Present Disclosure

Dimethicone, also known as polydimethylsiloxane or PDMS is a silicone-based polymer of varying size, based on the number of repeating units of the polymer. Dimethicones have wide ranging uses, for example in antiperspirants, skin creams, skin lotions, suntan lotions, bath oils, hair care products, and as coatings for oral products. Skin care products have a wide range of uses and dimethicone is relied upon for its properties as a base for a wide range of cosmetic formulations, its hydrophobicity, range of viscosities, lubricating properties, low surface tensions, clear, tasteless, odorless, inert, and that it is miscible with a wide range of other materials.

Indeed, dimethicones of various viscosity are relied upon in many cosmetic formulations where it is used for filling in uneven texture and fine lines, such as in primers, foundations, or lotions. Furthermore, as a silicone oil, it provides a protective cover on skin such as with suntan lotions or other skin lotions.

Dimethicones are also used in hair care products to provide smoothness, specifically in conditioners or detangling products. Indeed, the incorporation of dimethicone into said products assists with smoothing hair and providing ease for reducing or removing knots in hair. Furthermore, in many hair care products, dimethicones are utilized to leave a shine or sheen on hair.

PDMS has the typical formula:

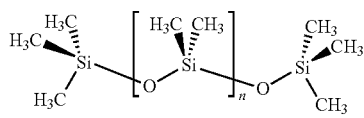

with the number of "n" repeating units impacting the viscosity of the material. Dimethicone products are often sold in various formulations by their viscosity. Here, we combine at least two different viscosity dimethicones, one having a viscosity of between about 1,000 cP and 25,000 cP and a second having a viscosity of between about 2.0 million cP and 3.0 million cP, and preferably about 2.5 million cP. When purchasing these materials, a typical certificate of analysis will provide a viscosity as determined by a rotational test, and each certificate of analysis will provide a specification limit for the material, usually within about 10%, or about 5%, or about 1% of a stated specification. For example, for a stated material having a 2.5 million cP viscosity, the materials used in the embodiments herein comprised a specification range of 2,312,500 to 2,687,500 cP.

The FDA has approved dimethicone for personal care products and generally is considered safe for use. Indeed, the FDA lists at least 16 entries for topical, transdermal, and oral applications. Of these four are specifically listed for oral applications, namely dimethicone 100, 350, 350, and 1000, with the duplicate 350 entries being one for a capsule and the other for a "capsule, sustained action." Accordingly, dimethicones have a known and expected safety profile with the FDA.

The difference in viscosity for dimethicone comes simply in the number of repeating polymer units of the molecule. For example, a polymer having a greater number of repeating units will tend to restrict movement and thus will have a greater viscosity than one with a lower number of repeating units. However, when purchasing these dimethicone products commercially, in nearly every example, the materials are sold by their viscosity, with a range or variation of about 1-10% of the stated viscosity.

In creating a formulation for the present oral varnish products, we needed to confirm all of the above considerations, namely: rate or release of active ingredients, adhesive forces, as well as the aesthetic and tactile response of the material to generate a superior product. As detailed in Formulations 1-9 below and in Table 3, we tested several different basic formulations, one using a 1,000 cP component with the 2.5 million cP dimethicone, and a second where the 1,000 cP dimethicone was replaced with a 12,500 dimethicone. We also tested variations using a 25,000, and 50,000 cP mixed with the 2.5 million dimethicone. Finally, we tested the 1,000 and 12,500 dimethicones with a lower 1.5 million cP dimethicone so as to evaluate the material in different concentrations and different base materials In sum, we found that use of a first dimethicone with a viscosity of less than 50,000 cP was more effective than those of 50,000 cP or greater, regardless of whether a 1.5 million, 2.0 million, 2.5 million, or 3.0 million cP viscosity second dimethicone was utilized. Furthermore, the difference in viscosity also appeared to be important, up to a point, namely that those using the 2.5 cP dimethicones functioned better than those mixed with the 1.5 million cP product. However, this is not to say that the 50,000 cP material, as the lower viscosity dimethicone, was not significantly more superior than the materials that are presently available. Accordingly, in the broadest sense, the combination of the two dimethicone materials, of varying viscosity, provides for significant advantages.

In a preferred embodiment, a first dimethicone of between 1,000 cP and 25,000 cP is admixed with a second dimethicone of 2.5 million cP and resulted in optimal retention and adhesion to the oral mucosa while also allowing for an appropriate feel, physical properties, and release profile.

Formulation of a Product for Oral Varnish Use

In creating an oral varnish formulation, typically, the formulation includes more than just the carrier and an active ingredient, and thus other suitable excipients are typically added to generate a particular formulation, or to improve the formulation, its consistency, viscosity, texture, taste, feel, or through inclusion of other active ingredients.

A primary active ingredient of the oral varnish is fluoride. Fluoride comes in several different forms, but it is provided in the dimethicone carrier to be placed in close proximity to tooth surfaces and, when the oral varnish is applied to and adhered to (or adjacent to) a tooth surface, will impart remineralizing properties, i.e. ions are deposited into demineralized enamel, including fluoride, calcium, and phosphate. For example, sodium fluoride is a common fluoride additive. Other fluorides known to those of skill in the art can also be utilized, for example stannous fluoride, ACP, ACPF, etc., are known and used in other oral care products. Each of these can be suitably added as a fluoride donor for remineralizing purposes, to allow for calcium, phosphate, and fluoride ions to be deposited into crystal voids in demineralized enamel.

Flavorant or sweeteners are frequently used in certain embodiments to provide for a pleasant taste when applying the material. In some embodiments described above, the tooth varnish compositions of the invention can further include one or more sweetening agents, flavoring agents, and coloring agents. Any suitable flavoring or sweetening material may be employed. Examples of suitable flavoring constituents includes natural or artificial tastes such as: natural flavorants, flavoring oils, e.g. including but not limited to: oil of spearmint, peppermint, wintergreen, clove, sage, eucalyptus, marjoram, cinnamon, citrus, vegetable, tree nut, fruit, and bramble. Other flavorants may include the oleoresin, essence or extractive, protein hydrolysate, distillate, or any product of roasting, heating or enzymolysis, which contain the flavoring constituents derived from a spice, fruit or fruit juice, vegetable or vegetable juice, edible yeast, herb, bark, bud, root, leaf or similar plant material, meat, seafood, poultry, eggs, dairy product, or fermentation products thereof, and other natural and synthetic flavoring agents as known to those of ordinary skill in the art.

Suitable sweetening agents include but are not limited to: nutritive and nonnutritive sweeteners, including sucrose, fructose, dextrose, high fructose corn syrup; sugar alcohols such as xylitol, maltitol, sorbitol, mannitol, erythritol; and artificial such as sucralose, aspartame, acesulfame potassium, saccharin, sedum saccharin and neotame; others may also include: lactose, maltose, sodium cyclamate, perillartine, AMP (aspartyl phenyl alanine methyl ester). Other natural and synthetic sweeting agents as known to those of ordinary skill in the art.

Suitably, flavor and/or sweetening agents may each or together comprise from up to 5%, or up to 4%, or up to 3%, or up to 2%, or up to 1%, or from 0.5% to 1%, by weight of the composition. In certain embodiments, providing a material without a flavorant or sweetener might be preferable, however the material may then have little to no flavor and might cause concern to patients that the material is not on a tooth surface. Accordingly, a small amount of either the sweetener or flavorant may help the patient understand that the material is present.

Addition of a bulking agent or texture. As with the inclusion of a flavorant, it may be suitable to provide a small amount of a bulking agent or texturizing agent to the product to impart mass and substance, impart a tactile feel to the material, or to improve its consistency for application to the tooth surfaces. For example, addition of natural or synthetic waxes, for example beeswax or a plant-based wax such as carnauba, candelilla, rice-based, or fruit-based waxes, edible waxes, fats, oils, Gantrez® (alternating units of methylvinylether and maleic anhydride), and other agents that can modify the flow, texture, and viscosity of the finalized product. Other bulking agents may include mannitol, dicalcium phosphate, calcium sulfate, dry starch, cellulose, kaolin, sodium chloride, anhydrous lactose, sorbitol, sucrose, and the like. Those of ordinary skill in the art recognize that bulking agents are frequently used in formation of pharmaceutical and oral products and thus understand the meaning of term as used herein. Preferably, when added, these agents are added at a concentration of between 0.1 to about 15% of the total weight of the composition.

Additionally, a flowing agent may be added to modify the final physical properties of the material to impart greater or lesser viscosity, or the ability of the product to flow or remain in its targeted position upon contact with aqueous saliva in the mouth. For example, magnesium stearate, stearic acid, silicon dioxide, glycerin, palmitate, and others known to those of ordinary skill in the art. Those of ordinary skill in the art recognize that flowing agents are frequently used in formulation of pharmaceutical products and thus understand the meaning of the term as used herein. Flowing agents are added at between about 0.1 to about 5% of the total weight of the composition.

Benzalkonium chloride may also be added as a therapeutic material, for its use as an antiseptic and disinfectant, and also for its preservative properties. However, when used in sufficient concentrations, its use as an antiseptic in the oral mucosa can help to reduce bacterial populations that may damage the oral mucosa. Other antibacterial agents may include, but are not limited to cetyl pyridinium chloride, trans-farnesol, chitosan, chlorhexidine, quaternary ammonium compounds, phenols, bisguanides, and combinations thereof. The antibacterial agents are added at between about 0.1 and 10% of the total weight of the composition.

A calcium donor, as used through, is a compound that allows for release of calcium ions from the composition. Those of ordinary skill in the art will recognize that calcium donors can be used in conjunction with a fluoride ion donor. The goal of providing both a fluoride and a calcium donor is to allow for greater remineralizing to tooth surfaces. Together, calcium and fluoride form an insoluble solid, calcium fluoride. The calcium donor is added at between about 0.1 and 10% of the total weight of the composition.

In certain embodiments, it may be suitable to add in a phosphate donor, including those such as ACP, Casein-phosphopeptide-ACP, phosphate monobasic, potassium phosphate dibasic, dicalcium phosphate, tricalcium phosphate, sodium phosphate monobasic, sodium phosphate monobasic, sodium phosphate dibasic, monomagnesium phosphate, dimagnesium phosphate, and other donors as known to those of ordinary skill in the art, their salts, and combinations thereof. The phosphate donor can be added at a concentration of about 0.1 to about 10% of the total weight of the composition.

Methods of Manufacture of the Dimethicone Oral Varnish Product

The mixture of two different viscosity dimethicone products, specifically of those having a difference in viscosity provides significant hurdles in manufacturing and mixing of components. Indeed, one cannot simply add all of the components to a mixing bowl and mix/stir the components to create the instant formulations. Several different protocols were tested to allow for thorough mixture of the components until an appropriate process was generated.

As an example, the components of Example 1 below, were tested in several different mixing applications. Initially, all components were placed together in a single mixing vessel and mixed with a magnetic stirring rod. Mixture was impossible due to the viscosity of the material. A further test attempted to use a spinning/rotating mixing blade. However, the viscosity of the material made this difficult, except for the smallest amounts of the 2.5 million cP material, and the blades introduced significant amounts of air into the product. This resulted in an unsuitable product. A further strategy was through the use of a bladeless mixing system that utilizes centrifugal forces to aid in mixing, and these strategies proved effective for mixing of the two different viscosity silicone materials and the additional excipients in the examples below.

EXAMPLES

Example 1

A Flacktek mixer was used to mix the following compounds: dimethicone (2.5 million cP); dimethicone (1,000 cP); sodium fluoride. Initially, 17.1 grams of 1,000 cP dimethicone was added to the mixing cup. Next 1 gram of sodium fluoride was added to the mixing cup. The two compounds were mixed at 3,000 RPM for 10 minutes. Next 1.9 grams of the 2.5 million cP dimethicone was added in five increments of 0.38 grams. After each increment was added, the formulation was mixed for and additional five-minute increment.

Subsequent formulation examples were prepared following the same procedure as Example 1. The following table lists the ratio of components used in the specific formulation example.

TABLE 1

| Formulation Example | Mass (g) of 1,000 cP Dimethicone | Mass (g) of 2.5 million cP Dimethicone | Mass (g) of Sodium Fluoride |
| --- | --- | --- | --- |
| 2 | 15.2 | 3.8 | 1 |
| 3 | 13.3 | 5.7 | 1 |
| 4 | 11.4 | 7.6 | 1 |
| 5 | 9.5 | 9.5 | 1 |

Example 6

A Flacktek mixer was used to mix the following compounds: dimethicone (2.5 million cP); dimethicone (12,500 cP); sodium fluoride. Initially, 17.1 grams of 12,500 cP dimethicone was added to the mixing cup. Next 1 gram of sodium fluoride was added to the mixing cup. The two compounds were mixed at 3,000 RPM for 10 minutes. Next 1.9 grams of the 2.5 million cP dimethicone was added in five increments of 0.38 grams. After each increment was added, the formulation was mixed for and additional five-minute increments.

TABLE 2

| Formulation | Mass (g) of 12,500 cP Dimethicone | Mass (g) of 2.5 million cP Dimethicone | Mass (g) of Sodium Fluoride |
|---|---|---|---|
| 7 | 15.2 | 3.8 | 1 |
| 8 | 13.3 | 5.7 | 1 |
| 9 | 11.4 | 7.6 | 1 |
| 9a | 18 | 1 | 1 |
| 9b | 18.5 | 0.5 | 1 |

The mucoadhesion of the nine dimethicone fluoride varnish formulations above were measured using the Tensile Test method as described in the literature. (Note that formulations 9a and 9b were not tested under this test). A Brookfield CT3 Texture Analyzer instrument was used at room temperature (23±1° C.). 20 grams of sample was used in a container and measurements were made within 2 minutes of filling the container. The Peak Adhesive Force was measured (n=6) for each formulation. These values are reported in Table 3 below. The Total Work of Adhesion was measured (n=6) for each fluoride varnish formulation. These values are reported in Table 3 below. A larger negative number indicates a greater peak Adhesive force, or a greater Total work of Adhesion.

TABLE 3

| Formulation | Peak Adhesive Force (N) | Total Work of Adhesion (N · sec) |
|---|---|---|
| 1 | −1.5 ± 0.03 | −0.68 ± 0.02 |
| 2 | −5.4 ± 0.15 | −2.0 ± 0.03 |
| 3 | −12.9 ± 1.2 | −5.3 ± 0.09 |
| 4 | −28.5 ± 2.7 | −10.8 ± 0.32 |
| 5 | −41.2 ± 1.7 | −16.5 ± 0.60 |
| 6 | −9.9 ± 0.33 | −3.7 ± 0.06 |
| 7 | −13.8 ± 0.28 | −6.6 ± 0.14 |
| 8 | −18.6 ± 1.7 | −10.9 ± 0.30 |
| 9 | −35.3 ± 4.0 | −16.0 ± 0.65 |

Example 10

A Flacktek mixer was used to mix the following compounds: dimethicone (2.5 million cP); dimethicone (1,000 cP); sodium fluoride; calcium nitrate. Initially, 9.3 grams of 1,000 cP dimethicone was added to the mixing cup. Next 1 gram of sodium fluoride was added to the mixing cup. Next, 0.2 grams of calcium nitrate was added to the mixing cup. The three compounds were mixed at 3,000 RPM for 10 minutes. Next 9.5 grams of the 2.5 million cP dimethicone was added in five increments of 1.9 grams. After each increment was added, the formulation was mixed for an additional five-minute increment.

Example 11

A Flacktek mixer was used to mix the following compounds: dimethicone (2.5 million cP); dimethicone (1,000 cP); sodium fluoride; calcium nitrate; potassium phosphate dibasic. Initially, 9.1 grams of 1,000 cP dimethicone was added to the mixing cup. Next 1 gram of sodium fluoride was added to the mixing cup. Next, 0.2 grams of calcium nitrate was added to the mixing cup. Next, 0.2 grams of potassium phosphate dibasic was added to the mixing cup. The four compounds were mixed at 3,000 RPM for 10 minutes. Next 9.5 grams of the 2.5 million cP dimethicone was added in five increments of 1.9 grams. After each increment was added, the formulation was mixed for five-minute increments.

Example 12

A Flacktek mixer was used to mix the following compounds: dimethicone (2.5 million cP); dimethicone (12,500 cP); sodium fluoride, calcium nitrate, potassium phosphate dibasic and spearmint oil. Initially, 9 grams of 1,000 cP dimethicone was added to the mixing cup. Next 1 gram of sodium fluoride was added to the mixing cup. Next, 0.2 grams of calcium nitrate was added to the mixing cup. Next, 0.2 grams of potassium phosphate dibasic was added to the mixing cup. Next, 0.1 grams of spearmint flavor was added to the mixing cup. The five compounds were mixed at 3,000 RPM for 10 minutes. Next 9.5 grams of the 2.5 million cP dimethicone was added in five increments of 1.9 grams. After each increment was added, the formulation was mixed for five-minute increments.

Example 13

A Flacktek mixer was used to mix the following compounds: dimethicone (2.5 million cP); dimethicone (12,500 cP); sodium fluoride; benzalkonium chloride. Initially, 9.3 grams of 1,000 cP dimethicone was added to the mixing cup. Next 1 gram of sodium fluoride was added to the mixing cup. Next, 0.2 grams of benzalkonium chloride was added to the mixing cup. The three compounds were mixed at 3,000 RPM for 10 minutes. Next 9.5 grams of the 2.5 million cP dimethicone was added in five increments of 1.9 grams. After each increment was added, the formulation was mixed for five-minute increments.

Additional Examples

Data from additional experiments using further compounds may be found in Table 4 below.

TABLE 4

| Formulation Example | Mass (g) of 1,000 cP Dimethicone | Mass (g) of 2,500,000 cP Dimethicone | Mass (g) of Sodium Fluoride | Mass (g) of Other Therapeutics | |
|---|---|---|---|---|---|
| 14 | 15 | 4 | 1 | Chitosan | 0.2 |
|  |  |  |  | Vanilla Flavor | 0.05 |
| 15 | 15 | 4 | 1 | Potassium Nitrate | 0.5 |
|  |  |  |  | Bubblegum Flavor | 0.05 |
|  |  |  |  | Sucralose | 0.05 |
| 16 | 15 | 4 | 1 | Cetylpyridinium Chloride | 0.2 |
|  |  |  |  | Xylitol | 0.05 |
|  |  |  |  | Caramel Flavor | 0.05 |
| 17 | 15 | 4 | 1 | Calcium Fluoride | 0.2 |
|  |  |  |  | Wintergreen Flavor | 0.05 |
|  |  |  |  | Chlorhexidine | 0.2 |
| 18 | 15 | 4 | 1 | Potassium Chloride | 0.2 |
|  |  |  |  | Trans-farnesol | 0.2 |
|  |  |  |  | Acesulfame K | 0.05 |
|  |  |  |  | Calcium Chloride | 0.2 |

DISCUSSION

As each of the formulations was evaluated, a pattern arose that upon mixing of more of the high viscosity 2.5 million cP dimethicone into the formulations, the ability to work with the material eroded based on an increase in the overall viscosity of the resultant formulation. Thus at the higher end of concentrations of the 2.5 million cP dimethicone, the resulting product was too viscous to apply to tooth surfaces with a standard applicator. By contrast, however, at a mixture of 1:4 (2.5 million: 1,000 cP), the mixture was easily applied to a sample tooth surface.

However, at a sample of 1:1 ratio, of the 1,000 cP and 2.5 million cP dimethicone, the viscosity of the material was increasingly difficult to utilize, and it was difficult to remove material from a tooth applicator. At mounts of greater than 1:4 1,000 cP to 2.5 million cP, the material becomes too viscous to apply with an applicator and to apply to the surface of the tooth. While at 1:1 ratio, the material would still be able to be applied to a tooth surface, it was not as easily workable as the lower ratio materials with regards to being applied as a liquid or gel like form. A formulation utilizing 90% of the 2.5 million cP dimethicone was attempted with a 1,000 cP in one test and with a 12,500 cP dimethicone in a second test. At these concentrations, the amount of the high viscosity dimethicone becomes too great and thus makes the material unworkable. Accordingly, amounts of less than 75%, less than 66%, less than 50%, etc. are preferred to provide a workable material. Any amount or percentage of between 1% and less than 80% of the 2.5 million cP dimethicone appears to be workable.

Accordingly, based on the data, an optimal formulation comprises between about 1% to about 66% of a high viscosity dimethicone (i.e. between 2 and 3 million cP), that is admixed with a low viscosity dimethicone (between 1,000 and 25,000 cP) and a fluoride donor. Optionally, further excipients can be added to meet certain flavor, aesthetic, tactile, and sensory requirements to improve the commercial uptake of the material. These components, and the proper ratio as described herein ensures that the material adheres to tooth surface.

In preferred embodiments, the oral varnish consists essentially of a first dimethicone material having a viscosity between 1,000 cP and 25,000 cP, and a second dimethicone material of between about 2.0 million and 3.0 million cP; and at least one active agent. In such embodiment, additional excipients may be advantageously added. Preferably, the first and second dimethicone are at a ratio of between 100:1 to 1:2 of the first to the second dimethicone material.

In a preferred embodiment an oral varnish consisting of a first dimethicone material having a viscosity between 1,000 cP and 25,000 cP, and a second dimethicone material of between about 2.0 million and 3.0 million cP; one active agent and one, two, or three additional excipients. Preferably, the first and second dimethicone are at a ratio of between 100:1 to 1:1 of the first to the second dimethicone material. More preferably, the first and second dimethicone are in a ratio of about 50:1 to about 2:1.

What is claimed is:

1. A method of formulating a dimethicone based oral varnish comprising a first dimethicone material having a viscosity between 1,000 cP and 25,000 cP, and a second dimethicone material having a viscosity of between about 2.0 million and 3.0 million cP and a fluoride donor, comprising adding the first dimethicone component into a mixing container and adding into it an amount of the fluoride donor; mixing the two components at 3,000 RPM for about 10 minutes in a centrifugal mixer, after the mixing step, adding into the mixed two components a portion of the second dimethicone, wherein a portion of the total mass of the second dimethicone added in at least two increments, each increment individually mixed at 3,000 RPM for five minutes before addition of a further increment, and adding a portion of the second dimethicone until all of the second dimethicone is added and mixed into the formulation.

2. The method of claim 1, further comprising at least one active ingredient.

3. The method of claim 1 wherein the one active ingredient comprises a calcium donor with the first dimethicone and the fluoride donor before mixing the components.

4. The method of claim 1 wherein the one active ingredient is an antimicrobial agent, and wherein the antimicrobial agent is added with the first dimethicone and fluoride donor before mixing the components.

5. The method of claim 1 further comprising adding a bulking agent, a flowing agent, a preservative, or combinations thereof with the fluoride donor.

6. The method of claim 3 wherein the antimicrobial agent is selected from the group consisting of: benzalkonium chloride, cetylphyrdimium chloride, and combinations thereof.

* * * * *